United States Patent [19]
Pitt et al.

[11] Patent Number: 5,476,653
[45] Date of Patent: Dec. 19, 1995

[54] POLYOXYMETHYLENE-OXYETHYLENE COPOLYMERS IN CONJUCTION WITH BIOMOLECULES

[75] Inventors: Colin G. Pitt, Westlake Village; Wayne Hendren, Thousand Oaks, both of Calif.

[73] Assignee: Amgen Inc., Thousand Oaks, Calif.

[21] Appl. No.: 409,630

[22] Filed: Mar. 22, 1995

Related U.S. Application Data

[63] Continuation of Ser. No. 900,037, Jun. 17, 1992, abandoned.

[51] Int. Cl.$^6$ .................................................. A61K 47/34
[52] U.S. Cl. .................... 424/78.3; 424/78.1; 525/54.1; 525/54.2; 525/54.3; 530/810
[58] Field of Search ........................... 424/78.3, 78.1, 424/54.1, 54.2, 54.3; 525/410; 528/403

[56] References Cited

U.S. PATENT DOCUMENTS

| | | | |
|---|---|---|---|
| 4,609,546 | 9/1986 | Hiratani | 424/83 |
| 4,917,888 | 4/1990 | Katre et al. | 514/12 |
| 5,013,556 | 5/1991 | Woodle et al. | 424/450 |
| 5,079,330 | 1/1992 | Makabe et al. | 525/403 |
| 5,153,265 | 10/1992 | Shadle et al. | 514/12 |

FOREIGN PATENT DOCUMENTS

| | | |
|---|---|---|
| WO90/04606 | 5/1990 | WIPO . |
| WO92/16484 | 10/1992 | WIPO . |

OTHER PUBLICATIONS

E. Franta, et al., "Model networks based on poly(1, 3–dioxolane)", *Makromol. Chem.*, 191, 1689–1698 (1990).
Abuchowski & Davis, "Soluble Polymers–Enzyme Adducts", in *Enzymes as Drugs*, Holcenberg & Roberts, ed, Wiley–Interscience, New York, N.Y., (1981) pp. 367–383.
Newmark et al., J. Appl. Biochem 4:185–189 (1982).
Katre et al., Proc. Natl. Acad. Sci USA 84: 1487–1491 (1987).
Fuertges and Abuchowski, J. Controlled Release 11:139–148 (1990).
Zalipsky et al., Eur. Polym. J., 19:1177–1183 (1983).
Fujita et al., J. Controlled Release, 11:149–156 (1990).
Veronese et al., J. Bioactive Comp Polym., 5:167–178 (1990).
Veronese et al., Appl. Biochem. Biotech., 11:141–152 (1985).
Franta et al., Die Makromol. Chem. 191:1689–1698 (1990).
Velichova et al., J. Polymer Science, Part A 28:3145–54 (1990).

*Primary Examiner*—Edward J. Webman
*Attorney, Agent, or Firm*—Daniel Chambers; Daniel R. Curry

[57] ABSTRACT

Biological factors with enhanced biological activity are prepared by covalently linking a biomolecule to one or more chains of a synthetic polymer wherein the synthetic polymer is derived from the oxymethylene-oxyethylene part structure.

21 Claims, 3 Drawing Sheets

Figure 3

POLYOXYMETHYLENE-OXYETHYLENE COPOLYMERS IN CONJUCTION WITH BIOMOLECULES

This application is a continuation of application Ser. No. 07/900,037, filed Jun. 17, 1992 which is hereby incorporated by reference, now abandoned.

The present invention relates to biological factors with enhanced activity comprising a biomolecule covalently linked to one or more synthetic polymers wherein the synthetic polymers are derived from the oxymethylene-oxyethylene part structure.

BACKGROUND OF THE INVENTION

Many biological molecules (biomolecules) which are administered for therapeutic purposes are rapidly cleared from the circulation by glomerular filtration and, as a consequence, exhibit relatively short-lived pharmacological activity. Because of this rapid clearance, it is often necessary to administer larger amounts of the biomolecule at more frequent intervals in order to achieve the requisite therapeutic response. It has been shown that the clearance time of such therapeutic agents can, in many cases, be increased by the covalent attachment of water-soluble polymers. Examples of such water-soluble polymers are polyethylene glycol, copolymers of ethylene glycol and propylene glycol, carboxymethyl cellulose, dextran, polyvinyl alcohol, polyvinyl pyrrolidone and polyproline [Abuchowski and Davis, Soluble Polymer-Enzyme Adducts. In: *Enzymes as Drugs*, Holcenberg and Roberts, eds., Wiley-Interscience, New York, N.Y., 1981, pp. 367–383; Newmark, et al., *J. Appl. Biochem.* 4:185–189 (1982); Katre, et al., *Proc. Natl. Acad. Sci. USA* 84:1487–1491 (1987)]. Conjugation with these polymers is claimed to increase the solubility of more hydrophobic drugs in water, eliminate aggregation of peptides and proteins and greatly reduce their immmunogenicity and antigenicity, and generally enhance the physical and chemical stability of therapeutic agents. Improved properties have been reported for proteins and peptides [Fuertges and Abuchowski, *J. Controlled Release*, 11:139–148 (1990)], low molecular weight therapeutics [Zalipsky et al, *Eur. Polym. J.*, 19:1177–1183 (1983)] and, more recently, for liposomes [Woodle, et al., U.S. Pat. No. 5,013,556, issued 7th May 1991].

Despite numerous positive reports, a review of the scientific literature shows that covalent binding to a synthetic water soluble polymer does not predictably enhance the biological activity of biomolecules. For example, conjugation of streptokinase-plasmin complex and Pluronic F68, a block copolymer of ethylene and propylene glycol, destroys the activity of this enzyme [Newmark, et al., *J. Appl. Biochem.* 4:185–189, (1982)]. Dextran conjugates of several proteins have been reported to be strongly immunogenic in rabbits, sheep and guinea pigs [Richter et al., *Int. Arch. Allergy*, 42:885–902 (1972)]. The plasma half-lives of dextran conjugates of uricase in mice depend on the charge of the dextran; cationic and neutral dextran accelerate the elimination of the protein, while anionic dextran increases the half-life [Fujita et al., *J. Controlled Release*, 11:149–156 (1990)]. Polyvinylpyrrolidone conjugates have been found to be immunogenic [Abuchowski and Davis, Soluble Polymer-Enzyme Adducts. In: *Enzymes as Drugs*, Holcenberg and Roberts, eds., Wiley-Interscience, New York, N.Y., 1981, pp. 367–383], and to destroy the biological activity of ribonuclease (Veronese, et al, *J. Bioactive Comp. Polym.*, 5:167–178 (1990)). In contrast, ribonuclease retains its activity after conjugation with polyethylene glycol (PEG) (Veronese, et al., *Appl. Biochem. Biotech.*, 11:141–152 (1985)]. Even the degree of substitution and type of conjugate linkage can impact on the biological activity of the biomolecule. For example, European patent application no. 0,335,423 A2, published on Apr. 10, 1989, discloses that progressive conjugation of cyanuric-chloride activated PEG to the protein granulocyte colony stimulating factor (G-CSF) proportionately reduces its biological activity in vitro. These examples teach that conjugation of biomolecules with a water soluble polymer is not a predictable means of improving the biological properties of therapeutic agents.

Poly-1,3-dioxolane is a synthetic water soluble polymer comprised of the formula $-[-O-CH_2-O-CH_2-CH_2-]_n-$. Poly-1,3,6-trioxocane, is a structurally related polymer with the formula $-[-O-CH_2-O-CH_2CH_2-O-CH_2CH_2-]_n-$. Here, n is the number of repeating mer units which can theoretically range from less than ten to many thousands. Both polymers contain the oxymethylene-oxyethylene part structure. Although polymers with this structure are known in the art [Franta, et al., *Die Makromol. Chem.* 191:1689–1698 (1990); Velichova, et al, *J. Polymer Science*, Part A, 28:3145–54 (1990)], none has heretofore been combined with biomolecules to enhance the activity of the latter.

A simple method of preparation of polymers containing the oxymethylene-oxyethylene part structure is ring-opening polymerization of the cyclic monomers 1,3-dioxolane or 1,3,6-trioxocane. The ratios of the methyleneoxy to ethyleneoxy groups in the resulting polymers, poly-1,3-dioxolane and poly-1,3,6-trioxocane, are 1:1 and 1:2, respectively. This ratio can be changed to a wide range of non-integer values by copolymerization of 1,3-dioxolane and 1,3,6-trioxocane with each other or with other monomers. For example, 1,3,5-trioxane, which has the formula $(CH_2O)_3$, has been copolymerized with either 1,3-dioxolane or 1,3,6-trioxocane to increase the methyleneoxy content of the polymer. Alternatively, copolymerization with oxirane may be used to increase the ethyleneoxy content. The conjugates of these oxymethylene-oxyethylene polymers with biological agents constitutes the present invention.

None of the previously described methods for preparation of polymer-conjugates adducts have disclosed details of how to modify a biomolecule with the subject polymers so that its biological activity in vivo is enhanced.

SUMMARY OF THE INVENTION

The present invention describes a new class of polymeric derivatives of biological agents having improved properties, such as greater stability, longer in vivo half-lives, reduced immunogenicity and antigenicity, and enhanced potency in mammals. The polymers consist of chains of oxymethylene and oxyethylene groups arranged in regular, random or block fashion. The ratio of oxyethylene to oxymethylene groups may vary widely and is determined by the choice of monomers used to prepare the polymer. Depending on the polymerization initiator and catalyst, the polymer may be unsubstituted at the chain ends or partially substituted at chain ends with an unreactive blocking group, such as an alkyl or aryl ether group. The water-soluble oxymethylene-oxyethylene copolymers having at least one terminal reactive group are conjugated to the functional groups of the biomolecule and the resulting adducts are purified to produce a modified biomolecule with extended circulating half-life and enhanced biological activity.

DETAILED DESCRIPTION OF THE INVENTION

The present invention relates to biological factors with enhanced biological activity comprising a biomolecule covalently linked to one or more polymers wherein the polymer contains the oxymethylene-oxyethylene part structure.

The biomolecules of the present invention include any molecule that has a significant biological activity, preferably in vivo activity, or is a carrier of molecules with significant biological activity. Biological activity means the ability to affect the occurrence, velocity, efficiency, and/or inhibition of any reaction taking place in a biological system, including binding of biological molecules to receptors and cellular responses to receptor binding. Biomolecules and carriers whose polymeric conjugates may exhibit enhanced biological activity are exemplified by, but not limited to proteins, polypeptides, liposomes and oligosaccharides. Among the more important proteins are (a) granulocyte colony stimulating factor (G-CSF), stem cell factor (SCF), erythropoietin (EPO) and other cytokines, (b) brain derived neurotrophic factor (BDNF) and other neurotrophic factors, (c) epidermal growth factor (EGF), keratinocyte growth factor(KGF) and other growth factors, (d) metalloproteinase inhibitor (MI), consensus interferon and other endogenous proteins that may have enzymatic activity or inhibit enzymatic activity in vivo.

The polymers of the present invention are composed of chains of oxymethylene and oxyethylene groups:

oxymethylene —[—O—CH$_2$]— oxyethylene —[O—CH$_2$—CH$_2$]—

As formulated, the polymer of the present invention can consist of a totally random sequence of oxymethylene and oxyethylene groups constituting the polymer chain. The polymer may also be derived from a regular sequence of oxymethylene and oxyethylene groups, such as the repeat group —O—CH$_2$—O—CH$_2$—CH$_2$—, in which case the oxymethylene and oxyethylene groups alternate throughout the chain. Alternatively, the polymer may be a block copolymer containing longer sequences of oxymethylene or oxyethylene groups, such as [—O—CH$_2$]$_n$— or —[O—CH$_2$—CH$_2$]$_n$—. Additionally, the polymer may be a combination of all of these molecular constructs. Preferably, oxymethylene repeat groups are present in the polymer in an amount of at least 10% by number, more preferably in an amount at least 25% by numbers and most preferably in an amount of about 50%.

A simple method of preparation of polymers containing the oxymethylene-oxyethylene part structure is ring-opening polymerization of the cyclic monomers 1,3-dioxolane or 1,3,6-trioxocane. The ratios of the methyleneoxy to ethyleneoxy groups in the resulting polymers, poly-1,3-dioxolane and poly-1,3,6-trioxocane, are 1:1 and 1:2, respectively. This ratio can be changed to a wide range of non-integer values by copolymerization of 1,3-dioxolane and 1,3,6-trioxocane with each other or with other monomers. For example, 1,3,5-trioxane, which has the formula (CH$_2$O)$_3$, could be copolymerized with either 1,3-dioxolane or 1,3,6-trioxocane to increase the methyleneoxy content of the polymer. Alternatively, copolymerization with oxirane may be used to increase the ethyleneoxy content.

Preferred polymers with random arrangements of the oxymethylene and oxyethylene groups may be prepared by cationic ring opening polymerization of pairs of cyclic monomers. Preferred cyclic monomers for this purpose are 1,3-dioxolane, 1,3,6-trioxocane, oxirane, and 1,3,5-trioxane, more preferably 1,3-dioxolane, 1,3,6-trioxocane, and 1,3,5-trioxane. These preferred monomers may be copolymerized in various combinations to form polymers, the most preferred of which are made up of monomer pairs such as oxirane with 1,3-dioxolane, 1,3-dioxolane with 1,3,5-trioxane, 1,3-dioxolane with 1,3,6-trioxocane, and 1,3,6-trioxocane with 1,3,5trioxane.

A most preferred embodiment is poly(1,3-dioxolane), where the oxymethylene content in the polymer chain is 50% by number, and the regular repeat sequence is —(OCH$_2$OCH$_2$CH$_2$)—. This polymer can be obtained by cationic ring-opening polymerization of 1,3-dioxolane according to known methods [Franta et al., *Die Makromol. Chem.*, 191:1689–1698 (1990)]. A second most preferred embodiment is poly(1,3,6-trioxocane), where the oxymethylene content is 33% by number, and the regular repeat sequence is —(OCH$_2$OCH$_2$CH$_2$OCH$_2$CH$_2$)—. This polymer can be derived by cationic polymerization of 1,3,6-trioxocane according to known methods [Velichova, et al, *J. Polymer Science*, Part A, 28:3145–54 (1990)]. A third most preferred embodiment is a polymer with a random sequence obtained by copolymerization of 1,3-dioxolane and 1,3,5-trioxane such that the oxymethylene content is approximately 80% by number. This polymer can be obtained as described in Example 1C.

Block copolymers may be prepared by initiating the polymerization of one monomer in the presence of a preformed polymer. For example, it is known that cationic polymerization of 1,3-dioxolane in the presence of commercially available hydroxy end-capped polyethylene glycol will lead to the formation of block copolymers [Reibel, et al, *Makromol. Chem. Macromol. Symp.* 3:221–230(1986)]. It is also known to polymer chemists that copolymerization of monomers with unequal reactivities will not result in completely random arrangements of the monomer groups, but instead can lead to polymers which contain long sequences of one or both mer groups.

The polymers of the invention are preferably of a size suitable for convenient attachment to a biomolecule and suitable for improving or enhancing the biological activity of the biomolecule. Suitable sizes for the polymers of the present invention are preferably less than 100,000 number average molecular weight, more preferably between 500 and 50,000 number average molecular weight, more preferably between 1,000 and 10,000 number average molecular weight.

Conjugation of the subject polymers to any biomolecule can be effected by methods that are generally known in the art. For example, the polymers may be conveniently attached to one or more reactive amino acid residues in a peptide or protein such as the alpha-amino group of the amino-terminal amino acid, the epsilon amino groups of lysine side chains, the sulfhydryl groups of cysteine side chains, the carboxyl groups of aspartyl and glutamyl sidechains, the alpha-carboxyl group of the carboxyl-terminal amino acid, tyrosine side chains, or to activated derivatives of glycosyl chains attached to certain asparagine, serine or threonine residues. A similar diversity of functional groups exist for conjugation with low molecular weight drugs. For example, PEG has been conjugated to penicillin V, aspirin, amphetamine, quinine and atropine using functionalities such as hydroxy, carboxyl, and amino groups [Zalipsky et al, Eur. Polym. J., 19:1177–1183 (1983)].

Numerous activated forms of the oxymethylene-oxyethylene polymers suitable for direct reaction with proteins may be employed. Useful functional groups for reaction with amino groups of biomolecules include active esters of carboxylic acid or carbonate derivatives, particularly those in which the leaving groups are N-hydroxysuccinimide, p-nitrophenol, or 1-hydroxy-2-nitrobenzene-4-sulfonate. Polymer derivatives containing maleimido or haloacetyl groups are useful reagents for the conjugation of free sulfhydryl groups. Likewise, reagents containing amino, hydrazine or hydrazide groups are useful for reaction with aldehydes generated by periodate oxidation of carbohydrate groups of biomolecules.

It is important that the number of activated groups on the oxymethylene-oxyethylene polymer be controlled. Conjugation via a single end group of the polymer chain is preferred, particularly if the biomolecule has more than a single functional group capable of conjugation; the reaction of a multifunctional polymer with multifunctional biomolecule can potentially produce uncontrollable concatenation and crosslinked products. The preparation of a polymer with a single reactive group is achieved by the polymerization conditions, specifically the choice of catalyst and the initiator. The use of alcohols as initiators for ring opening polymerization of monomers such as 1,3-dioxolane and 1,3,6-trioxocane in the presence of a trifluoromethysulfonic acid catalyst affords polymers containing one hydroxy end group and one alkoxy end group [Franta, et al, Die Makromol. Chem. 191:1689–1698 (1990)]. The use of methyl fluorosulfonate or methyl triflate as the catalysts for the polymerization of 1,3-dioxolane leads to a polymer, α-methoxy-ω-hydroxy-poly(1,3-dioxolane), containing one methoxy and one hydroxy end group [Yokoyama, et al., Polymer J., 11:365–370 (1979)].

It is also known to polymer scientists that the molecular weight of the product will be directly related to the molar amount of alcohol employed by the formula $M_n=[ROH]^{-1}$. Furthermore, the use of polyhydric alcohols permits the preparation of branched polymers containing oxomethylene and oxyethylene chains.

The number of reactive groups in a biomolecule, their spatial distribution with respect to receptor-binding sites, and their importance in maintaining the native configuration and biological activity vary from compound to compound. For these reasons, it is not generally possible to predict a priori the extent of modification or sites of polymer attachment that will produce the optimum longer-lived conjugate without destroying its desired biological activity.

The modified biological factors, comprising a biomolecule covalently linked to one or more polymer chains, can be used for improving or enhancing the biological activity of the biomolecule. Improving the biological activity of a biomolecule can include increasing its specific activity, increasing its circulating half-life, decreasing its clearance, decreasing its susceptibility to enzymatic degradation, increasing its absorption, increasing its physical and thermal stability, reducing its antigenicity, or increasing its solubility.

Administration of the modified biological factors of the present invention involves administration of an appropriate amount of a pharmaceutical composition containing the modified biological factors as an active ingredient. In addition to the active ingredient, the pharmaceutical composition may also include appropriate buffers, diluents and additives.

Administration may be by any conventional means including but not limited to intravenously, subcutaneously, or intramuscularly.

Preferably, the pharmaceutical preparation is in unit dosage form. In such form, the preparation is subdivided into unit doses containing the appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. The amount and frequency of administration will be regulated according to the judgment of the attending clinician considering such factors as age, condition and size of the patient as well as severity of the disease being treated.

EXAMPLES

The following examples are provided as specific embodiments of the present invention and are not intended to limit its scope in any way.

EXAMPLE 1

Preparation of Polymers

Poly (1,3-dioxolane) and poly (1,3,6-trioxocane) were prepared by cationic homopolymerization of 1,3-dioxolane and 1,3,6-trioxocane, respectively, according to a procedure described by Franta et al. [Die Makromolek Chem. 191:1689–1698 (1990)]. Copolymers of 1,3-dioxolane and 1,3,6-trioxocane with each other and with 1,3,5-trioxane were prepared by the same procedure, employing mixtures of the appropriate monomers. Polymer end-groups and molecular weights were controlled by the choice of catalyst and initiator.

A. α-Ethoxy-ω-hydroxy-poly (1,3-dioxolane)

Methylene chloride (26.9 g) and 1,3-dioxolane (32.5 g) were dried by standing over calcium hydride overnight, then distilled under nitrogen into a glass vessel containing the initiator 2-(2-ethoxyethoxy)ethanol (0.62 g) and the catalyst triflic acid (30 mL). Polymerization was conducted at 50° C. After 5 hr, 1 mL of aqueous potassium hydroxide was added and the mixture was shaken, then poured into cold ether. The precipitated polymer was filtered, dried in vacuo, and characterized by NMR and IR spectroscopy and gel permeation chromatography. The melting point was 44° C. Intrinsic viscosity [η]=0.273 (CHCl$_3$). The $^1$H-NMR spectrum showed major peaks at 4.76 (—O—CH$_2$—O—) and 3.73 ppm (—O—CH$_2$CH$_2$—O—), ratio 2:4, and minor peaks due to the ethoxy end group at 1.21 (t,J=7Hz, —CH$_3$) and 3.53 (q,J=7Hz, —OCH$_2$—). IR (liquid film) peaks occurred at 3550 cm$^{-1}$ (OH end group); GPC (ultrastyragel, CHCl$_3$, polyethylene glycol standards) M$_n$=5400, M$_w$/M$_n$=1.71.

α-Methoxy-ω-hydroxy-poly (1,3-dioxolane) was prepared by substituting methyl triflate for triflic acid, and omitting 2-(2-ethoxyethoxy)-ethanol.

B. Poly ( 1,3,6-trioxocane )

1,3,6-Trioxocane was prepared from the reaction of formaldehyde and diethylene glycol in toluene in the presence of Amberlite IR-120 (Rohm and Haas Co.), following a procedure described by Astle et al. [*Ind. Eng. Chem.*, 46(4):787–91 (1954)]. Polymerization of 1,3,6-trioxocane (15.5 g) was performed in dry nitromethane (22.2 g) at 50° C., using 2-(2-ethoxyethoxy)ethanol (0.20 g, 1.48 mmol) as the initiator and trifluoromethanesulfonic acid (100 μl, 1.13 mmol) as the catalyst. After 15 min, the mixture was quenched with t-butylamine and the product was isolated by precipitation with ether. The precipitated polymer(13.3 g, 86%) was filtered, dried in vacuo, and characterized by NMR and IR spectroscopy and gel permeation chromatography. Intrinsic viscosity [η]=0.31 (CHCl$_3$). The $^1$H-NMR spectrum showed major peaks at 4.74 (—O—CH$_2$—O—) and 3.69 ppm (—O—CH$_2$CH$_2$—O—), ratio 2:8, and a minor peak due to the ethoxy end group at 1.21(t, J=7Hz, CH$_3$). An IR (liquid film) peak occurs at 3550 cm$^{-1}$ (OH end group); GPC (ultrastyragel, CHCl$_3$, polyethylene glycol standards) M$_n$=7440, M$_w$/M$_n$=1.51.

C. Copolymer of 3-dioxolane and 1,3,5-trioxane

Methylene chloride (28 g) and 1,3-dioxolane (37.0 g) were dried by standing over calcium hydride overnight, then distilled under nitrogen into a glass vessel containing 1,3,5-trioxane (45.0 g), the initiator 2-(2-ethoxyethoxy) ethanol (0.62 g) and the catalyst triflic acid (30 μL). Polymerization was conducted at 50° C. After 5 hr, 1 mL of aqueous potassium hydroxide was added and the mixture was shaken, then poured into cold ether. The precipitated polymer was filtered, dried in vacuo, and characterized by NMR and IR spectroscopy and gel permeation chromatography. Intrinsic viscosity [η9 =0.3 (CHCl$_3$). The $^1$H-NMR spectrum showed major peaks at 4.76 (—O—CH$_2$—O—) and 3.73 ppm (—O—CH$_2$CH$_2$—O—) , ratio 8:4, and minor peaks due to the ethoxy end group at 1.21 (t,J=7 Hz, —CH$_3$) and 3.53 (q,J=7Hz, —OCH$_2$—) . IR (liquid film) 3550 cm$^{-1}$ (OH end group); GPC (ultrastyragel, CHCl$_3$, polyethylene glycol standards) M$_n$=5000, M$_w$/M$_n$=1.7.

EXAMPLE 2

Preparation of Activated Polymers

A. Succinimidyl α-Ethoxy-poly(1,3-dioxolane)-ω-carbonate

α-Ethoxy-ω-hydroxy-poly(1,3-dioxolane) (3.5 g, 0.65 mmole) and N,N'-disuccinimidylcarbonate (716 mg, 2.80 mmole) were dissolved in anhydrous DMF( 20 mL), followed by dropwise addition of dimethylaminopyridine (512 mg, 4.19 mmole) in anhydrous DMF (10 mL) . The reaction mixture was stirred for 1 hr at room temperature, then slowly added to anhydrous ether (300 mL) at 4° C. The precipitate was collected by filtration, redissolved in anhydrous DMF and recovered again by precipitation in anhydrous ether to yield 3 g.

The succinimidyl content of this and other succinimidyl esters was determined spectroscopically. Approximately 2–3 mg of the product was accurately weighed and diluted with 100 mM bicine buffer, pH 8.0, to obtain a concentration of 1 mg/mL. The UV absorbance at 260 nm was monitored in a 1 cm cuvette as a function of time until a constant absorbance was obtained. The amount of succinimidyl ester was calculated from the difference in the initial (A$_o$) and final (A$_∞$) absorbances, and the known extinction coefficient of 8760 M$^{-1}$cm$^{-1}$ of N-hydroxysuccinimide.

B. Succinimidyl αEthoxy-poly(1,3-dioxolane)-ω-glutarate

α-Ethoxy-ω-hydroxy-poly (1,3-dioxolane), (2.7 g, 0.50 mmole), glutaric anhydride (285 mg, 2.50 mmole), dimethylaminopyridine (244 mg, 2.01 mmole) and triethylamine (0.28 mL, 2.01 mmole) were dissolved in anhydrous dioxane (25 mL). After standing overnight at room temperature, the product was recovered by dropwise addition of the reaction mixture to cold ether and cyclohexane (2:1,300 mL). The precipitate was filtered and dried in vacuo to yield 2.5 g. This intermediate glutarate half ester (2.5 g, 0.45 mmole) was dissolved in anhydrous dichloromethane (20 mL), and N-hydroxysuccinimide (0.12 g, 1.0 mmole) and dicyclohexylcarbodiimide (0.207 mg, 1.00 mmole) were added. The solution was left overnight at room temperature, after which the precipitated dicyclohexylurea was removed by filtration and washed with dichloromethane. The filtrate, concentrated by evaporation, was added to cold anhydrous ether/cyclohexane (2:1, 300 mL). The precipitated product was purified by reprecipitation from anhydrous DMF with ether/cyclohexane to yield 2.2 g.

C. Succinimidyl α-Ethoxy-ω-carboxymethyl-poly (1;3-dioxolane)

α-Ethoxy-ω-hydroxy-poly(1,3-dioxolane) (5 g, 0.09 mmole) was dissolved in anhydrous toluene (20 mL) and potassium t-butanoate (1.6 g, 14 mmole) was added. The solution was brought to reflux, then kept at 50° C. for 5 h. Ethyl bromoacetate (1.6 mL, 14 mmole) was slowly added and the solution was stirred overnight at the same temperature. The precipitated salts were removed by filtration and washed with methylene chloride (20 mL). The polymer was recovered by partially concentrating the filtrate and slowly pouring into ether/cyclohexane (1:1, 200 mL). The polymer was dried in vacuo, then dissolved in 1N NaOH (20 mL) and NaCl (4 g) was added. After 1 hour, this solution was acidified with 2N HCl to pH 3.0 and extracted with dichloromethane (3×50 mL). The combined organic phase was dried (MgSO$_4$), concentrated to 30 mL, and poured into cool ether/cyclohexane (3:1, 300 mL) . The precipitate was collected by filtration and dried in vacuo.

The resulting α-ethoxy-ω-carboxymethyl-poly(1,3-dioxolane), (5 g, 0.09 mmole) was dissolved in anhydrous dichloromethane (20 mL) , and N-hydroxysuccinimide (0.23 g, 2.0 mmole) and dicyclohexylcarbodiimide (0. 413 g, 2.00 mmole) were added. The solution was left overnight at room temperature, after which the precipitated cyclohexylurea was removed by filtration and washed with dicloromethane. The solution was concentrated and added to cold anhydrous ether/cyclohexane (1:1, 300 mL). The product was purified by precipitation from solution in anhydrous DMF with ether/cyclohexane to yield 4.8 g.

D. Succinimidyl ω-Ethoxypoly(1,3-dioxolane)-ω-succinate.

α-Ethoxy-ω-hydroxy-poly(1,3-dioxolane), (5.4 g, 0.09 mmole), succinic anhydride (125 mg, 1.25 mmole), dimethylaminopyridine (122 mg, 1.00 mmole) and triethylamine (0.14 mL, 1.00 mmole) were dissolved in anhydrous dioxane (30 mL) and left overnight at room temperature. The solvent was evaporated, the residue taken up in carbon tetrachloride (15 mL), filtered and precipitated in cold ether (300 mL). The precipitate was filtered and dried in vacuo.

The yield was 5.14 g. To this intermediate (5 g) in anhydrous DMF (25 mL) was added N-hydroxysuccinimide (126 mg, 1.09 mmole), followed by dicyclohexylcarbodiimide (227 mg, 1.10 mmole) in anhydrous DMF (1 mL). The mixture was left at room temperature overnight, filtered and the polymer recovered by precipitation in cold anhydrous ether(250 mL). Dissolution in anhydrous DMF and precipitation in ether was repeated twice to yield 4 g.

E. Succinimidyl α-Ethoxy-ω-carboxymethyl-poly(1,3,6-trioxocane)

α-Ethoxy-ω-hydroxy-poly ( 1,3,6-trioxocane) (7.5 g, 1.0 mmole) was dissolved in anhydrous t-butanol (50 mL) at 50° C. and potassium t-butanoate (1.6 g, 14 mmole) was added. The solution was stirred at 50° C. for 8 h. Ethyl bromoacetate (1.6 mL, 14 mmole) was slowly added and the solution stirred overnight at the same temperature. The precipitated salts were removed by filtration and washed with methylene chloride (20 mL). The polymer was recovered by partially concentrating the filtrate and slowly pouring into ether (300 mL). The precipitated polymer was dried in vacuo, then dissolved in 1N NaOH (30 mL) and NaCl (6 g) was added. After 4 h the solution was acidified with 2N HCl to pH 3.0 and extracted with dichloromethane (3×50 mL). The combined organic phase was dried ($MgSO_4$), concentrated to 25 mL, and poured into cold ether(300 mL). The precipitate was collected by filtration and dried in vacuo.

The resulting carboxymethyl derivative (5.9 g) was dissolved in anhydrous dichloromethane (20 mL), and N-hydroxysuccinimide (0.18 g, 1.6 mmole) and dicyclohexylcarbodiimide (0.33 mg, 1.6 mmole) were added. The solution was left overnight at room temperature, after which the precipitated cyclohexylurea was removed by filtration and washed with dichloromethane. The solution was concentrated and added to cold anhydrous ether(300 mL). The product was purified by reprecipitation to yield 4.9 g.

EXAMPLE 3

Conjugation of the Polymer to Protein.

A. Conjugation of Poly(1,3-dioxolane) to G-CSF

Succinimidyl α-ethoxypoly(1,3-dioxolane)-ω-succinate (540 mg; 80.6 μmol; $M_n$=6,700), prepared as described in Example 2D, was added to 3.0 mL of a solution containing 30.3 mg (1.61 μmol) of recombinant human granulocyte colony stimulating factor (rhuG-CSF) in 0.10M sodium borate, pH 9.0. The solution was stirred at room temperature for 30 minutes, then diluted with 27 mL of 0.10M sodium citrate, pH 3.25, and concentrated (Amicon Centriprep 10 centrifugal ultrafilter) to a final volume of approximately 2 mL. The concentrated crude reaction mixture was applied to a gel filtration column (Pharmacia Superdex Prep 200, 1.6×60 cm) and eluted with 0.10M sodium citrate, pH 3.25, at a flow rate of 0.25 mL/min. Protein in the column effluent was monitored continuously (UV absorbance at 280 nm), and fractions (1.0 mL) were collected. Fractions no. 18–57, which contained the predominant portion of modified protein, were pooled, dialyzed by ultrafiltration (Amicon YM10 membrane) against water for injection (WFI), titrated to pH 3.25 with HCl, and concentrated by ultrafiltration to a final protein concentration of 1.2 mg/mL (calculated from $A_{280}$ using the rhuG-CSF value of $A_{280}$=0.86 for a 1.0 mg/mL solution). Under similar gel filtration chromatography conditions, unmodified rhuG-CSF eluted in fractions no.77 to 84.

B. Conjugation of Poly(1,3-dioxalane) to G-CSF

Succinimidyl α-ethoxypoly(1,3-dioxolane) -ω-carbonate (437 mg; 65.2 μmol; $M_n$=6,700), prepared as described in Example 2A, was added to 1.23 mL of a solution containing 24.5 mg (1.30 μmol) of rhuG-CSF in 0.10M sodium borate, pH 9.0. The solution was stirred at room temperature for 2 hours, then diluted with 11 mL of 0.10M sodium citrate, pH 3.25, and 49 mL of water for injection (WFI). The diluted crude reaction mixture was applied to a cation exchange column (Pharmacia S-Sepharose, 1.5×2.3 cm) which had been pre-equilibrated with 20 mM sodium citrate, pH 3.25. Once the entire reaction mixture was adsorbed, the column was washed with 8 mL of 20 mM sodium citrate, pH 3.25, to elute the reaction by-products, N-hydroxysuccinimide and a-ethoxypoly (1,3-dioxolane )-ω-carbonate. Adsorbed protein was then eluted with 24 mL of 20 mM sodium citrate, pH 3.25, 1M NaCl, dialyzed by ultrafiltration (Amicon YM10 membrane) against WFI, titrated to pH 3.25 with HCl, and concentrated by ultrafiltration to a final protein concentration of 1.1 mg/mL (calculated from $A_{280}$ using the rhuG-CSF value of $A_{280}$=0.86 for a 1.0 mg/mL solution). Reaction products were analyzed by size-exclusion HPLC on TosoHaas TSK G3000SWXL and TSK G4000SWXL columns connected in series (each 0.78×30 cm; 5μ), eluting with 0.1M sodium phosphate, pH 6.9, at a flow rate of 1 mL/min; the effluent was monitored continuously with ultraviolet (280 nm) and refractive index detectors. The final product was free of unbound poly-1,3-dioxolane and unmodified rhuG-CSF.

C. Conjugation of Poly(1,3-dioxolane) to Stem Cell Factor

Succinimidyl α-ethoxy-ω-carboxymethyl-poly (1,3-dioxolane) , 4.2 mg (0.793 μmol), prepared as described in Example 2C, was added to 7.25 mg (0.396 μmol) of recombinant rat stem cell factor(rr-SCF) in 0.725 mL of 0.1M bicine buffer, pH 8.0, at room temperature. After one hour the reaction mixture was diluted with 2.9 mL of WFI, titrated to pH 4.0 with 1.0 N HCl, and filtered through a 0.20μ cellulose acetate filter (Nalgene no. 156–4020). The filtrate was applied at a rate of 4.0 mL/min to a 6.0×1.6 cm column of Toyopearl SP550C (Toso-Haas) which had been previously equilibrated with 20 mM sodium acetate, pH 4.0 at room temperature. Effluent from the column was collected in 2.5-mL fractions (no.1–2) during sample loading, and the ultraviolet absorbance ($A_{280}$) of the effluent was monitored continuously. The column was then sequentially washed with 24.0 mL of the equilibration buffer at 4.0 mL/min (fractions no. 3–12), with 48.0 mL of 20 mM sodium acetate, 0.3M NaCl, pH 4.0 at 4.0 mL/min (fractions no. 13–31), and finally with 24.0 mL of 20 mM sodium acetate, 1.0M NaCl, pH 4.0 at 8.0 mL/min (fractions no. 32–41). Fractions (no. 16–23) containing the polymer-rr-SCF conjugate were combined, dialyzed by ultrafiltration (Amicon YM-10 membrane) against 10 mM sodium acetate, 140 mM NaCl, pH 5.0, and sterilized by ultrafiltration (0.45 μ cellulose acetate membrane; Costar no.8302) to yield 4.0 mg of final product in a volume of 6.13 mL.

D. Conjugation of Poly(1,3-dioxolane) to SCF

Succinimidyl α-ethoxy-ω-carboxymethyl-poly(1,3-dioxolane), 19.4 mg (3.66 μmol), prepared as described in Example 2C, was added to 6.70 mg (0.366 μmol) of rr-SCF in 0.67 mL of 0.1M bicine buffer, pH 8.0, at room temperature. After one hour the reaction mixture was diluted with 2.68 mL of WFI, titrated to pH 4.0 with 1.0N HCl, filtered through a 0.20μ cellulose acetate filter (Nalgene no. 156–4020), and applied at a rate of 4.0 mL/min to a 6.0×1.6 cm column of Toyopearl SP550C (Toso-Haas) which had been previously equilibrated with 20 mM sodium acetate, pH 4.0, at room temperature. Effluent from the column was collected in 2.5 mL fractions (no. 1–2) during sample loading, and the ultraviolet absorbance ($A_{280}$) of the effluent was monitored continuously. The column was then sequentially washed with 24.0 mL of the equilibration buffer at 4.0 mL/min (fractions no. 3–12), with 48.0 mL of 20 mM sodium acetate, 0.3M NaCl, pH 4.0 at 4.0 mL/min (fractions no. 13–31), and finally with 24.0 mL of 20 mM sodium acetate, 1.0M NaCl, pH 4.0 at 8.0 mL/min (fractions no. 32–41). Fractions (no. 15–19) containing the polymer-rr-SCF conjugate were combined, dialyzed by ultrafiltration (Amicon YM-10 membrane) against 10 mM sodium acetate, 140 mM NaCl, pH 5.0, and sterilized by ultrafiltration (0.45 μcellulose acetate membrane; Costar no.8302) to yield 3.26 mg of final product in a volume of 6.94 mL.

E. Conjugation of Poly ( 1,3,6-trioxocane) to SCF

Succinimidyl α-ethoxy-ω-carboxymethyl-poly (1,3,6-trioxocane) (4.6 mg; 0.794 μmol), prepared as described in Example 2E, was added to 7.26 mg (0.397 μmol) of rr-SCF in 0.726 mL of 0.1M bicine buffer, pH 8.0, at room temperature. After one hour the reaction mixture was diluted with 2.90 mL of WFI, titrated to pH 4.0 with 1.0N HCl, and filtered through a 0.20μ cellulose acetate filter (Nalgene no. 156–4020). The filtrate was applied at a rate of 4.0 mL/min to a 6.0×1.6 cm column of Toyopearl SP550C (Toso-Haas) which had been previously equilibrated with 20 mM sodium acetate, pH 4.0 at room temperature. Effluent from the column was collected in 2.5 mL fractions (no. 1–2) during sample loading, and the ultraviolet absorbance ($A_{280}$) of the effluent was monitored continuously. The column was then sequentially washed with 24.0 mL of the equilibration buffer at 4.0 mL/min (fractions no. 3–12), with 48.0 mL of 20 mM sodium acetate, 0.3M NaCl, pH 4.0 at 4.0 mL/min (fractions no. 13–31), and finally with 24.0 mL of 20 mM sodium acetate, 1.0M NaCl, pH 4.0 at 8.0 mL/min (fractions no. 32–41). Fractions (no. 16–26) containing the polymer-rr-SCF conjugate were combined, dialyzed by ultrafiltration (Amicon YM-10 membrane) against 10 mM sodium acetate, 140 mM NaCl, pH 5.0, and sterilized by ultrafiltration (0.45μ cellulose acetate membrane; Costar no.8302) to yield 3.47 mg of final product in a volume of 7.15 mL.

F. Conjugation of Poly(1,3,6-trioxocane) to SCF

Succinimidyl α-ethoxy-ω-carboxymethyl-poly(1,3,6-trioxocane) (24.3 mg; 4.19 μmol), prepared as described in Example 2E, was added to 7.67 mg (0.419 μmol) of rr-SCF in 0.767 mL of 0.1M bicine buffer, pH 8.0, at room temperature. After one hour the reaction mixture was diluted with 3.07 mL of WFI, titrated to pH 4.0 with 1.0N HCl, and filtered through a 0.20 μcellulose acetate filter (Nalgene no. 156–4020). The filtrate was applied at a rate of 4.0 mL/min to a 6.0×1.6 cm column of Toyopearl SP550C (Toso-Haas) which had been previously equilibrated with 20 mM sodium acetate, pH 4.0 at room temperature. Effluent from the column was collected in 2.5 mL fractions (no. 1–2) during sample loading, and the ultraviolet absorbance ($A_{280}$) of the effluent was monitored continuously. The column was then sequentially washed with 24.0 mL of the equilibration buffer at 4.0 mL/min (fractions no. 3–12), with 48.0 mL of 20 mM sodium acetate, 0.3M NaCl, pH 4.0 at 4.0 mL/min (fractions no.13–31), and finally with 24.0 mL of 20 mM sodium acetate, 1.0M NaCl, pH 4.0 at 8.0 mL/min (fractions no. 32–41). Fractions (no. 15–19) containing the polymer-rr-SCF conjugate were combined, dialyzed by ultrafiltration (Amicon YM-10 membrane) against 10 mM sodium acetate, 140 mM NaCl, pH 5.0, and sterilized by ultrafiltration (0.45μ cellulose acetate membrane; Costar no.8302) to yield 5.85 mg of final product in a volume of 7.62 mL.

EXAMPLE 4

Enhancement of Biological Activity by Conjugation

A. In Vivo Activity of ω-ethoxypoly(1,3-dioxolane) conjugates with G-CSF

Figure 1:
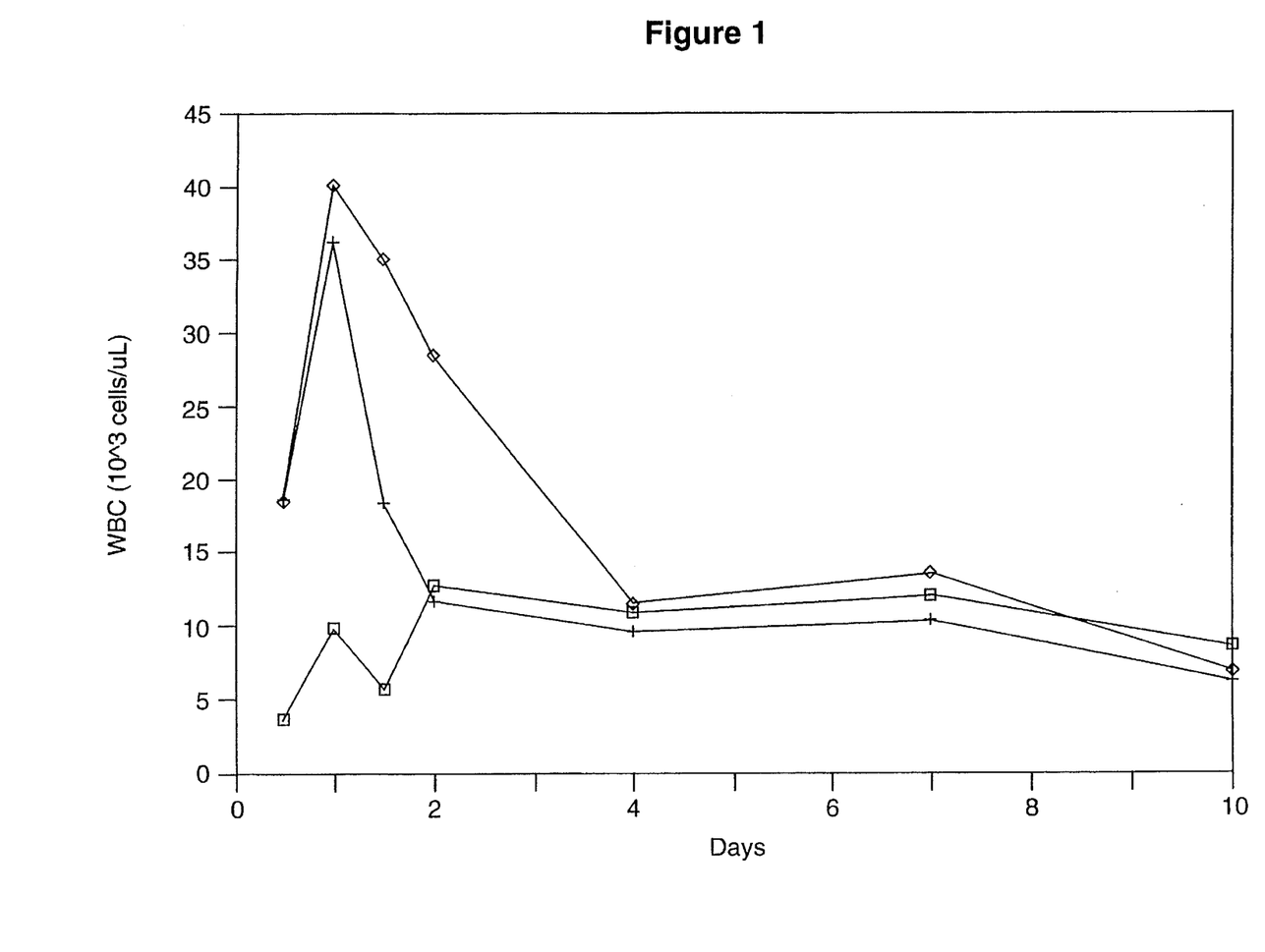
FIG. 1. Circulating white blood cell levels in hamsters following a single subcutaneous injection of 100 μg/kg of rhuG-CSF (+), 100 μg/kg of α-ethoxypoly (1,3-dioxolane)-ω-succinate-rhuG-CSF, Example 3A, (-◊-), or placebo (-0-).
Figure 2:
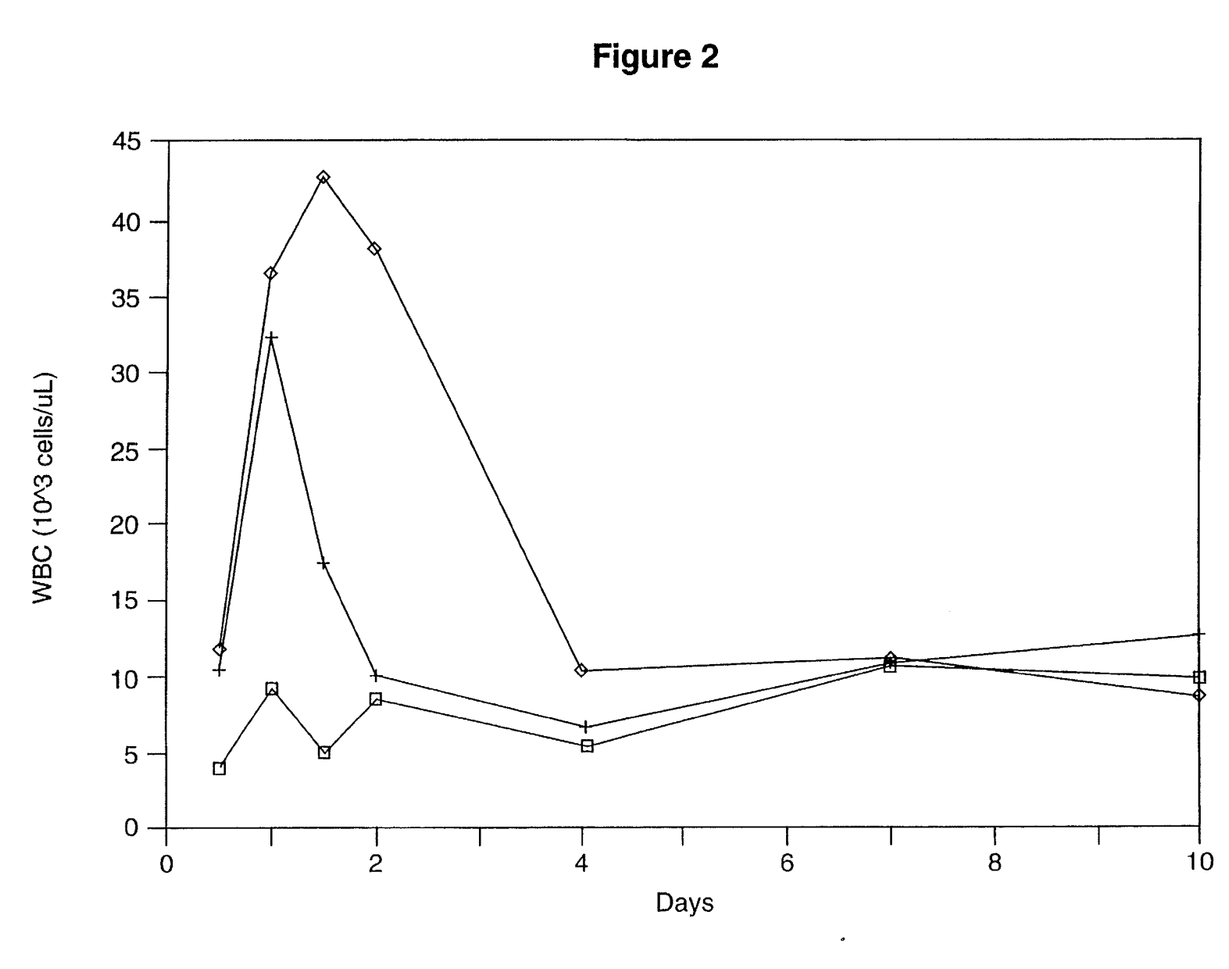
FIG. 2. Circulating white blood cell levels in hamsters following a single subcutaneous injection of 100 μg/kg of rhuG-CSF (+), 100 μg/kg of α-ethoxypoly (1,3-dioxolane)-ω-carbonate-rhuG-CSF, Example 3B, (-◊-), or placebo (-0-).

The poly (1,3-dioxolane)-rhuG-CSF conjugates described in Examples 3A and 3B were compared with unmodified rhuG-CSF in an in vivo hamster granulopoiesis bioassay. Each test material, poly(1,3-dioxolane)-rhuG-CSF conjugate, unmodified rhuG-CSF or placebo, was injected subcutaneously into 35 male Golden Syrian hamsters (90–110 g) in a single dose of 100 μg protein/kg body weight. Terminal blood samples were obtained by cardiac puncture from five animals in each treatment group at intervals of 0.5, 1, 1.5, 2, 4, 7 and 10 days after dosing, and total white blood cell (WBC) counts were measured. WBC levels in animals treated with the poly(1,3-dioxolane)-rhuG-CSF conjugates remained elevated two days after dosing, at which time WBC levels in animals treated with unmodified rhuG-CSF had returned to normal (FIGS. 1 and 2).

Figure 3:
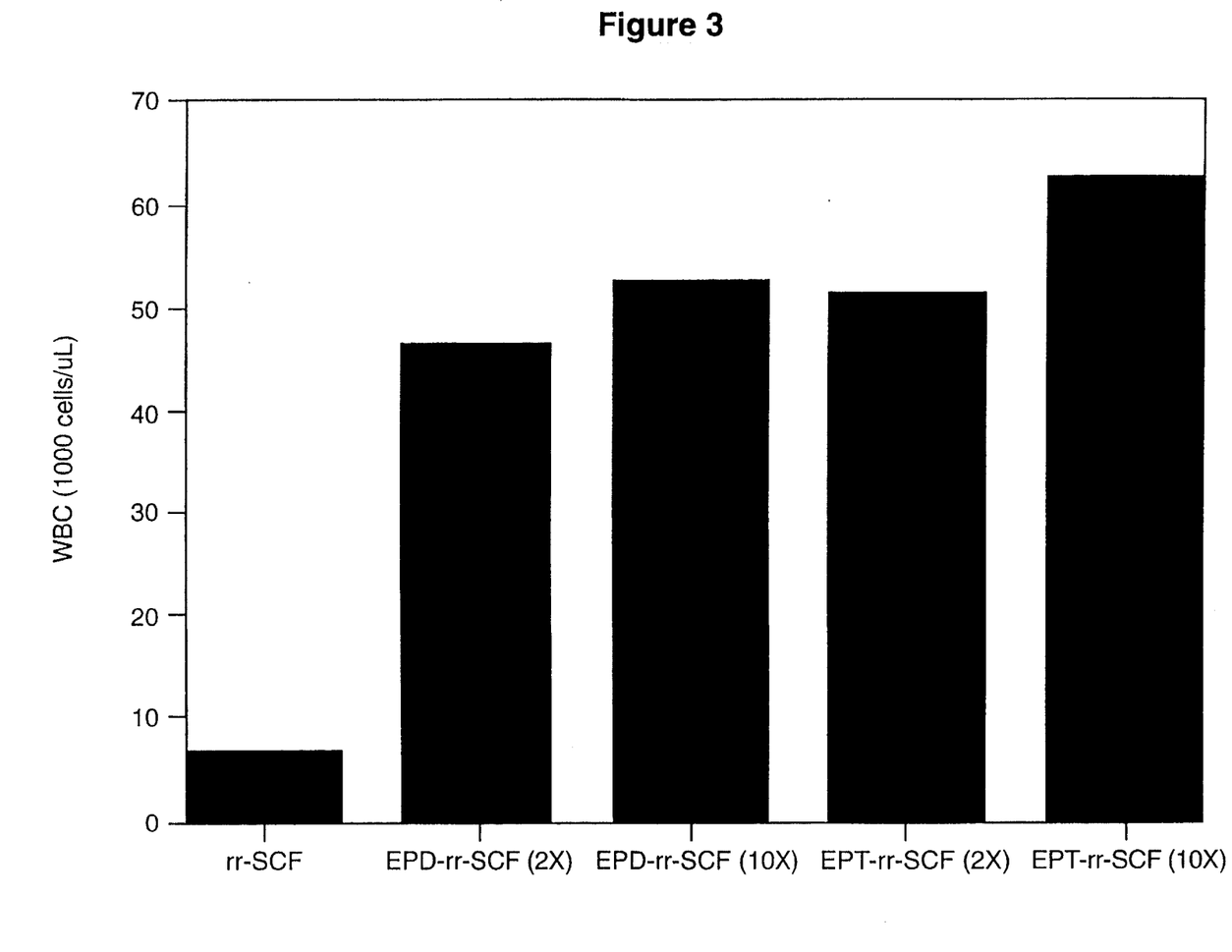
FIG. 3. Circulating white blood cell levels in mice following seven daily subcutaneous injections of 1 mg/kg of rr-SCF, 1 mg/kg of α-ethoxy-ω-carboxymethylpoly (1,3-dioxolane)-rr-SCF [EPD-rr-SCF (2X), Example 3C; EPD-rr-SCF (10X), Example 3D], 1 mg/kg of α-ethoxy-ω-carboxymethyl-poly(1,3,6-trioxocane)-rr-SCF [EPT-rr-SCF (2X), Example 3E; EPT-rr-SCF (10X), Example 3F], or placebo (-0-).

B. Biological Activity of ω-ethoxypoly(1,3,6-trioxocane) and ω-ethoxypoly(1,3-dioxolane) conjugates with SCF Poly(1,3-dioxolane) and poly(1,3,6-trioxocane) conjugates of recombinant rat SCF, prepared as described in Examples 3C–3D and 3E–3F, respectively, were administered daily to female Swiss ICR outbred mice (Charles River Breeding Laboratories CD-1; 22–24 g) at a dose of 1.0 mg/kg for a period of seven consecutive days. Each treatment group consisted of five animals. Dosing solutions were prepared by diluting the polymer-protein conjugates in 10 mM sodium acetate, 0.14M NaCl, 0.5 mg/mL mouse serum albumin, pH 5.0, and were administered by subcutaneous injection in a volume of 0.2 mL. On the eighth day of the study, blood samples were obtained from each mouse by nicking the lateral tail vein with a sterile scalpel and collecting a 0.02 mL aliquot of blood with a disposable pipet. Blood samples were immediately diluted with an anticoagulant solution and counted with an 8-parameter automatic blood analyzer (Model HC-820; Danam Electronics, Dallas, Tex.). White blood cell levels were markedly elevated in mice treated with the polymer-rr-SCF conjugates, compared with mice treated with unmodified rr-SCF (FIG. 3).

What is claimed is:

1. A composition of matter comprising a first component and a second component, the first component selected from the group consisting of a biologically active molecule and a carrier of a biologically active molecule wherein said carrier carries a biologically active molecule, and the second component consisting of a linear polymer chain of oxymethylene and oxyethylene monomers wherein the second component is covalently linked to the first component.

2. A composition of matter according to claim 1 wherein the polymer chain containing between 10% and 90% of polymerized oxymethylene monomers by number.

3. A composition of matter according to claim 1 wherein the polymer chain contains 50% of polymerized oxymethylene monomers by number.

4. A composition of matter according to claim 1 wherein the polymer chain contains about 33% of polymerized oxymethylene monomers by number.

5. A composition of matter according to claim 1 wherein the polymer chain contains a —O—CH$_2$—O—CH$_2$—CH$_2$—repeat.

6. A composition of matter according to claim 1 wherein the polymer chain contains a —O—CH$_2$—O—CH$_2$—CH$_2$—O—CH$_2$—CH$_2$—repeat.

7. A composition of matter according to claim 1 wherein the polymer chain contains random polymers of oxymethylene and oxyethylene monomers.

8. A composition of matter according to claim 1 wherein the polymer chain contains blocks of polymerized oxymethylene monomers and polymerized oxyethylene monomers.

9. A composition of matter according to claim 1 wherein the polymer chain contains both random and block polymers of oxymethylene and oxyethylene monomers.

10. A composition of matter according to claim 1 wherein the first component is selected from the group consisting of a polypeptide, a carbohydrate, and a liposome.

11. A composition of matter according to claim 1 wherein the first component is a protein.

12. A composition of matter according to claim 11 wherein the protein is a hematopoietic growth factor.

13. A composition of matter according to claim 12 wherein the hematopoietic growth factor is selected from the group consisting of EGF, EPO, GM-CSF, G-CSF, PDGF, MI, consensus interferon and SCF.

14. A composition of matter according to claim 1 wherein the monomers of the polymer chain are selected from the group consisting of 1,3-dioxolane, 1,3,6-trioxocane, oxirane, 1,3,5-trioxane and mixtures thereof.

15. A composition of matter according to claim 1 wherein the polymer chain has a number average molecular weight between 500 and 100,000.

16. A composition of matter according to claim 15 wherein the polymer chain has a number average molecular weight between 500 and 100,000.

17. A composition of matter according to claim 1 wherein the polymer chain is attached to the first component via reaction with an active ester of a carboxylic acid or carbonate derivative of said polymer.

18. A composition of matter according to claim 1 wherein the polymer chain is attached to the first component via reaction with a member selected from the group consisting of an ester of N-hydroxysuccinimide, an ester of p-nitrophenol, and an ester 1-hydroxy-2-nitro-benzene-4-sulfonate, attached to the polymer.

19. A composition of matter according to claim 1 wherein the polymer chain is attached to the first component via reaction of one or more free sulfhydryl groups of the first component and a maleimido or haloacetyl derivative of the polymer.

20. A composition of matter according to claim 1 wherein the polymer chain is attached to the first component via reaction of a member selected from the group consisting of an amino, a carboxyl, a sulfhydryl and a hydroxyl group of the first component.

21. A composition of matter according to claim 1 wherein the polymer chain is attached to the first component via reaction with a member selected from the group consisting of an amino, a hydrazino and a hydrazido derivative of the polymer chain and one or more aldehyde groups on the first component generated by oxidation of the carbohydrate moieties of the first component.

* * * * *

UNITED STATES PATENT AND TRADEMARK OFFICE
CERTIFICATE OF CORRECTION

PATENT NO. : 5,476,653

DATED : December 19, 1995

INVENTORS : Colin G. Pitt and Wayne Hendren

It is certified that error appears in the above-identified patent and that said Letters Patent is hereby corrected as shown below:

On the title page, item

[54] TITLE, Line 2, change "CONJUCTION" to --CONJUNCTION--.

Column 1, Line 2, change "CONJUCTION" to --CONJUNCTION--.

Column 4, Line 2, change "numbers to --number,--.

Column 4, Line 29, change "1,3,5trioxane" to --1,3,5-trioxane--.

Column 7, Line 31, change "3-dioxolane" to --1,3-dioxolane--.

Column 7, Line 42, change "$[\eta^9$" to --$[\eta]$--.

Column 8, Lines 29-30, change "(1;3-dioxolane)" to --(1,3-dioxolane)--.

Column 11, Lines 9-10, change "0.45 µcellulose" to --0.45µ cellulose--.

Column 13, Line 27, in claim 16, change "500 and 100,000" to --1,000 and 10,000--.

Signed and Sealed this

Fourteenth Day of December, 1999

Attest:

Q. TODD DICKINSON

*Attesting Officer*  Acting Commissioner of Patents and Trademarks